United States Patent [19]
Stearns et al.

[11] Patent Number: 5,532,599
[45] Date of Patent: Jul. 2, 1996

[54] HIGH VOLTAGE SPARK EXCITATION AND IONIZATION SYSTEM INCLUDING DISC DETECTOR

[76] Inventors: Stanley D. Stearns, 1201 Archley Dr., Houston, Tex. 77055; Wayne E. Wentworth, 614 E. Larkspur Cir., Pearland, Tex. 77584

[21] Appl. No.: 349,495

[22] Filed: Dec. 2, 1994

Related U.S. Application Data

[63] Continuation-in-part of Ser. No. 662,149, Feb. 28, 1991, Pat. No. 5,153,519, and a continuation-in-part of Ser. No. 956,632, Oct. 5, 1992, Pat. No. 5,317,271, and a continuation-in-part of Ser. No. 176,968, Jan. 3, 1994, Pat. No. 5,394,092, and a continuation-in-part of Ser. No. 201,467, Feb. 25, 1994, Pat. No. 5,394,090, and a continuation-in-part of Ser. No. 201,469, Feb. 25, 1994, Pat. No. 5,394,091.

[51] Int. Cl.$^6$ ............................ G01N 27/62; G01N 27/68
[52] U.S. Cl. ............................ 324/464; 324/455; 73/28.02
[58] Field of Search ............................ 324/123 R, 71.4, 324/449, 450, 452, 464; 73/28.02, 23.35; 436/153; 313/231.41, 231.71; 315/111.01, 111.91; 250/379, 385.2, 382

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |
| 5,338,931 | 8/1994 | Spangler et al. | 250/287 |
| 5,394,090 | 2/1995 | Wentworth et al. | 324/464 |
| 5,394,091 | 2/1995 | Wentworth et al. | 324/464 |
| 5,394,092 | 2/1995 | Wentworth et al. | 324/464 |

OTHER PUBLICATIONS

A Compilation of Research on Pulsed Discharge Detectors, Article, Summary of Paper Presented at the Pittsburgh Conference, 1994 month unavailable.

Introduction to: Pulsed Discharge Helium Ionization Detector, Reprint of Publication in the Journal of Chromatographia, vol. 34, No. 5–8, pp. 219–115 (1992) month unavailable.

Introduction to: Pulsed Discharge Electron Capture Detector Reprint devoted solely to the PDECD (J of Chromatogra. Sci., vol. 30, pp. 478–485, (1992) month unavailable.

Pulsed Discharge Helium Ionization Detector, W. E. Wentworth, S. V. Vasnin, Stearns, & Meyer, Chromatographia, vol. 34, No. 5–8, Sep./Oct. 1992.

Pulsed Discharge Photoionization Detector (PDPID), A Summary of a paper presented at the 1994—Pittsburgh Conference by W. E. Wentworth month unavailable.

Pulsed Discharge Emission Detector–Application to Analytical Spectroscopy of Permanent Gases, Vasnin, Wentworth, Stearns & Meyer, Chromatographia, vol. 34, No. 5–8, Sep./Oct. 1992.

Pulsed Discharge Helium Ionization Detector, A Universal Detector for Inorganic and Organic Compounds at the Subpicogram Level, Wentworth, et al, Version of 5/25 (undated).

Reprinted from Process Control & Quality, 5 (1993) 193–204, Elsevier Science B.V., Amsterdam, Pulsed–Discharge Helium Ionization/Electron Capture/Emission Detector of Chlorinated Compounds, Wentworth, et al Jan. 1993.

Environmental Applications of the Pulsed–Discharge Electron–Capture Detector, Wentworth, D'Sa & Cai, Journal of Chromatographic Science, vol. 30, Dec. 1992.

Introduction to: Pulsed Discharge Emission Detector (PDED) Chromatographia, vol. 34, pp. 226–234, (1992) month unavailable.

Primary Examiner—Kenneth A. Wieder
Assistant Examiner—Diep Do
Attorney, Agent, or Firm—Gunn & Associates

[57] ABSTRACT

A circular chamber is disclosed. Helium is introduced into the chamber to swirl in a circle to flow past a pair of spaced electrodes forming a spark in the helium. The chamber enables a sample detected by interaction with spark initiated ionization.

16 Claims, 2 Drawing Sheets

FROM GAS SOURCES 26 & 26'

HIGH VOLTAGE SPARK EXCITATION AND IONIZATION SYSTEM INCLUDING DISC DETECTOR

This disclosure is a continuation in part of application Ser. No. 662,149 which was filed on Feb. 28, 1991 and which issued as U.S. Pat. No. 5,153,519 on Oct. 6, 1992, and application Ser. No. 956,632 which was filed on Oct. 5, 1992, now issued as U.S. Pat. No. 5,317,271 on May 31, 1994, and application Ser. No. 176,968 which was filed on Jan. 3, 1994, now U.S. Pat. No. 5,394,092 and also application Ser. No. 201,467, now U.S. Pat. No. 5,394,090 and application Ser. No. 201,469, now U.S. Pat. No. 5,394,091, both filed Feb. 25, 1994.

BACKGROUND OF THE DISCLOSURE

The present disclosure is directed to a system for making several charged species by a pulsed DC spark discharge acting on an inert gas, typically helium, which utilizes the charged species to classify and/or quantify compounds in a gas sample. This detector is connected with upstream or downstream devices such as a sample source, gas chromatography (GC) column, spectrum analyzers, etc. Understanding of various test procedures will illuminate use of the described apparatus and can be gained from review of the apparatus and its mode of operation in a system. A sample to be evaluated is first loaded along with a carrier gas into a system column. The sample passes through this device, a pulsed, high voltage discharge, and several types of detection systems are initiated by this detector. For instance, the very short DC spark creates a readily available thermalized electron flux which can be used in a detection system. In an alternate mode of operation, the spark also creates a more slowly diffused flux of metastable helium atoms which drift toward into a gas sample at a controlled rate. The helium atoms will react with molecules of the gas sample to surrender the excess energy from the excited state to cause sample molecule ionization which, as a secondary reaction, can be measured by a detection system. Another aspect involves transitory photo ionization of a gas into positive and negative charged particles normally recombining at high speed. If a selected bias voltage is applied, the recombination is prevented to furnish a current signal indicative of gas contents.

The preferred form of this system features a pulsed DC spark discharge in the inert gas flow which is followed by a comparably slow metastable carrier gas dispersion and secondary reaction, which is slow in contrast with the practically instantaneous electron initiated interaction the time of the spark. The DC spark discharge therefore enables various detection mechanisms, as will be explained, so that variations in detection electrode geometry and pulse timing can obtain different types of responses. One system uses the highly mobile electron flux while an alternate system relies on the metastable carrier gas molecular energy interchange occurring well after the electron flux. An electron capture detector is set forth. Also, an air monitor is disclosed.

In addition to the particle interaction initiated in the spark manifest in different aspects, there are also two electrode systems responsive to the DC spark. From the spark gap, the electron discharge creates charged species which can be observed at spaced electrodes. Geometry of the spark is sharply defined, narrowly confined, and repetitively located.

This device enables detection of the atomic species in the gas sample. While a first spectrum is formed only during the spark, a second spectral analysis is enabled by the subsequent decay of the metastable helium atoms giving up their excess energy by ionizing molecules of the sample. This interchange occurs as the energized helium atoms diffuse from the spark gap in the test chamber and mix with the sample molecules. Dependent on relative concentrations, diffusion and flow rates, the sample molecules are ionized to emit energy characteristic of the species. This delayed emission is useful in species identification when timely observed, and therefore a different mode of observation is used capture data from this emission. This difference in operation derives primarily from delayed occurrence and is observed at a different time.

The present invention uses to advantage a simple spark gap having a pair of spaced electrodes connected to a current pulse forming system. The pulses are narrow, preferably as small as a fraction of a microsecond. The DC pulses repetitively form precise, sharp and well defined transgap sparks, liberating the electron flux mentioned and also forming the metastable helium molecules. The spark is fixed in size and relative timing, shape and location. Electrode geometry does not erode with time and electron ejection is uniform. Thus, the spark is fixed for observation by spectral analysis. Structurally, this enables a very simple chamber to deploy a pair of opposing, spaced electrodes in a cavity of small volume with gas flow inlet and outlet ports. In a representative system, a chemical sample is mixed with a carrier gas. The sample is prepared for testing by classification, identification or quantification using the detector. An exemplary system achieves separation as a result of differences in travel time through a GC column input to the detector. As is well known, the GC column is either a wall coated open capillary or packed with a stationary phase material so that the carrier gas and the compounds making up the sample are eluated from the GC column. As a generalization, the mobile phase (usually a flowing gas) is delivered by the GC column into this detector for detection of the separated chemical constituents making up the sample.

The detector is operated periodically to test every sample constituent compound passing through the detector. One type of detector used in the past has been the electron capture detector (ECD). The present disclosure sets out an alternate form of ECD detector used in conjunction with a GC column which forms an output signal of substantial sensitivity. The present system features an ECD with a DC pulsed, high voltage spark discharge. As noted at column 2 of U.S. Pat. No. 4,851,683, DC discharges have been known, but they generally have had in homogeneous excitation characteristics and are unstable because of electrode heating and erosion. U.S. Pat. No. 4,509,855 is a DC atmospheric pressure helium plasma emission spectrometer. Additional devices are shown in U.S. Pat. No. 4,866,278. The present apparatus sets forth a DC pulsed, high voltage, spark discharge source which provides a repetitive uniform spark. The spark has a duration which is only a fraction of a microsecond. It would appear theft an acceptable spark duration is a fraction of a microsecond. Moreover, the spark gap is structurally fixed to have a finite width for discharge of the spark created by accumulating energy in a reactive circuit such as a coil and capacitor charging. Preferably, a non-ringing current is applied.

This detector in a representative form includes a means for forming a stabilized spark gap so that the spark and resultant charged particle population are uniform in contrast with the problems referenced in the two mentioned patents. Accordingly, the carrier gas (e.g., carrier flow from the GC column) is directed as a gas flow through appropriate tubing into the spark chamber. An inert gas flows in the spark chamber past a pair of electrodes which are arranged to direct the spark transverse to the inert gas flow. In a first mode of operation, a flux of electrons is obtained. These electrons are quickly dissipated during the spark interval even when spark duration is only a fraction of a microsecond. The number of electrons available can be measured by means of an electrometer connected to electrodes spaced remotely from the spark gap. The electrometer circuitry connected with an electrode in the chamber and spaced from the spark gap detects and measures the electron flux resulting from the spark discharge. In this instance, the spark gas initiates an ECD operation. There is, however, a timed charged particle flux which is delayed after the spark discharge which uses an ionization mode. This involves a delay of up to about 100 or even 200 microseconds after the spark discharge creates ionized molecules which are dispersed at a slower rate compared with the more mobile electron dispersal. The spark disperses highly energized electrons during the spark and also creates a second and slower dispersion of metastable inert gas molecules (preferably helium) after the spark. Charged particle dispersal of the first form is, as a practical matter, instantaneous while metastable helium dispersal is time delayed. The two types of dispersion are readily identified because they involve different types of particles. The dispersal of metastable helium atoms, with an elevated energy state of about twenty or more eV, can be observed at a distance from the spark gap so that sample compound concentration (a scale factor) in the chamber is measured. The metastable helium concentration is useful because it enables this delayed reactions. Thus, the metastable helium atoms react with the sample molecules input with the carrier flow. The high energy in the helium ionizes the sample molecules, creating a measurable current in the chamber.

Building on the last possibility, metastable helium molecules may combine with a trace constituent such as a dopant supplied with the inert (helium) gas. One such dopant is nitrogen which, in reaction with the metastable helium, forms nitrogen ions. That causes liberation of electrons which again, because of different mobility, dissipate more readily. Before the electrons recombine with the ionized nitrogen molecules, they will react with the compounds making up the sample flowing through the detector. A connected electrode and electrometer measures electron capture from the dopant involvement to define an electron capture detector.

Another alternate form of apparatus involves observation of the spectrum. This involves the conversion of the certain constituents to elevated energy states where emissions occur at characteristic frequencies, and such frequencies can be observed and measured. This typically involves a spectrum analyzer such as a spectrometer which observes one or more atomic or molecular emission lines in selected regions of the spectrum. Spectral line observation varies with the time relative to the spark discharge. Regarding time, the observed spectrum is different during and after the spark discharge. The present apparatus is therefore summarized as a pulsed DC spark discharge where the spark discharge reacts with an inert gas (preferably helium) to detect compounds in a sample. In this spark, charged particles are created, the particles being either disassociated electrons, an ionized inert gas, ionized dopant gas, or highly energized helium atoms in a metastable form. Depending on the timing of measurements, the particular ionized particles and measurement voltages applied, the device can be operated in an ionization mode, or electron capture mode. Molecules of a compound separated by chromatographic separation or other input devices can be quantified. The device also emits characteristic spectral lines depending on the nature and timing of the emission. Moreover, by selection of the dopant gas, control of pulsing of the spark gap forming the charged particles, timed operation of measurement electrodes, and adjustment of scale factors, it is possible to operate in several modes. In addition to this, precisely defined spectral lines can be observed.

The present apparatus additionally includes simplified versions of the pulse discharge mechanism cooperative with a GC system. In one instance, the helium metastable molecule is used to achieve ionization of the eluate from the GC column without forcing the eluate to flow through the spark gap. This enhances operation of the equipment because the spark acts primarily on helium, while the electrodes are protected from contamination by the solvent or the eluate sample flowing from the GC column. In this version of equipment, the GC column discharge is delivered into the chamber at a location where it is not required to flow through the spark gap. As a second alternative, a dopant gas is input to the detector. Further, this type arrangement enables the system to operate as a simple ionization detector. Alternately, it can be operated as an electron capture detector (ECD hereafter). Details of these structures will be given later. Another aspect of the present apparatus is the use of the device to form an emission spectra which provides spectra from various samples through a transparent window. In this aspect of the system, it is provided with a transparent window sealed at the entrance of a monochromator. In this aspect of the invention, the helium gas flow plus the eluate from the GC column is across the transparent window so that the reaction products do not contaminate the window which loses transparency as a result of impinging contamination. So to speak, the window is located to view the mixing. Through the use of this mechanism spectral emissions can be obtained to analyze the constituent components of a sample. For instance, characteristic atomic, ionic, or molecular spectra lines can be classified. One characteristic of the atomic spectra is formation of extremely narrow emission lines with little or no interference between spectra from other atoms or molecules. This is especially helpful in the vacuum ultraviolet region. By contrast, the ultraviolet and visible regions of the spectra may receive broad interfering spectra from many common elements or molecules. Accordingly, it is especially desirable to operate in the vacuum ultraviolet region and in particular the region of about 120–200 nanometers.

ADVANTAGES OF THE IMPROVED DETECTOR

The present detector is constructed to utilize circular flow patterns within a cylindrical housing. In contrast with the structure set forth in the related disclosures which show linear gas flow through a structure in the preferred embodiments, this preferred embodiment has a cylinder which is constructed with an internal cavity. The flowing carrier gas and eluated molecules from the GC are introduced at a tangent and are directed in a circle. The circular flow enables the detector to segregate particles based on the weight of the molecules. The heavier molecules flow at the outer cylindrical surface and lighter molecules flow at the center of the structure. Rotation is imparted because the inlet carrier gas and eluated molecules from the GC are directed into the structure at a tangent imparting circular or rotating motion. Restated, one aspect and one important advantage of the present system is an arrangement which directs the GC carrier gas and eluated molecules in a circular pathway. This permits the molecules to flow at a relatively fixed distance from the spark gap which is arranged at the center of the cylinder. The heavier eluated gas is segregated away from the spark gap by centrifugal forces thereby minimizing corrosion of the spark electrodes. The spark gap forms the necessary metastable molecules or electron emission which interacts with the eluated compounds. A fixed exposure is achieved. Moreover, the eluated compounds interact with a pair of ring shaped concentric electrodes. These two electrodes function as a bias electrode and a collecting electrode. One is connected with a fixed voltage to provide a bias. The other is connected with an electrometer so that a current flow is established indicative of the concentration of the compound eluated from the GC column.

A further advantage is that circular flow retains eluted gas within the detector for a relatively long period of time when compared with previously mentioned linear flow detectors. This, in turn, yields a more precise and accurate measurement as will be detailed in a following section.

In other aspects, the circular structure is particularly advantageous. It can be used with or connected to an air inlet, not a GC column. It can be used to detect trace gases in the air. As an air detector, a reduced size is then provided. A portable structure is then defined. The structure is particularly advantageous in portable applications such as monitoring fugitive gas discharges which might reach excessive levels in the atmosphere.

In one particular aspect of the present disclosure, the circular detector housing can be made relatively small, having a diameter of up to about 3 or 4 centimeters, and a thickness of approximately 1.5 centimeters or less. The internal cavity is preferably provided with a cylindrical outer wall which creates centrifugal rotation of the gases in the structure. The chamber is ideally maintained at approximately atmospheric pressure. There is no need to make an expensive housing capable of withstanding substantial pressure differentials. A vent is provided out of the chamber, and discharges the chamber which is continuous in operation so long as input gas is delivered to the chamber.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 3 is a sectional view through the detector assembly in exploded view to show assembly of the collecting electrode and bias electrode and detector housing members which telescope together to form a closed housing; and FIG. 4 is a side view of one half of the detector housing showing a tangent passage which provides for centrifugal gas rotation within the detector.

DETAILED DESCRIPTION OF THE PREFERRED EMBODIMENT

Figure 1:
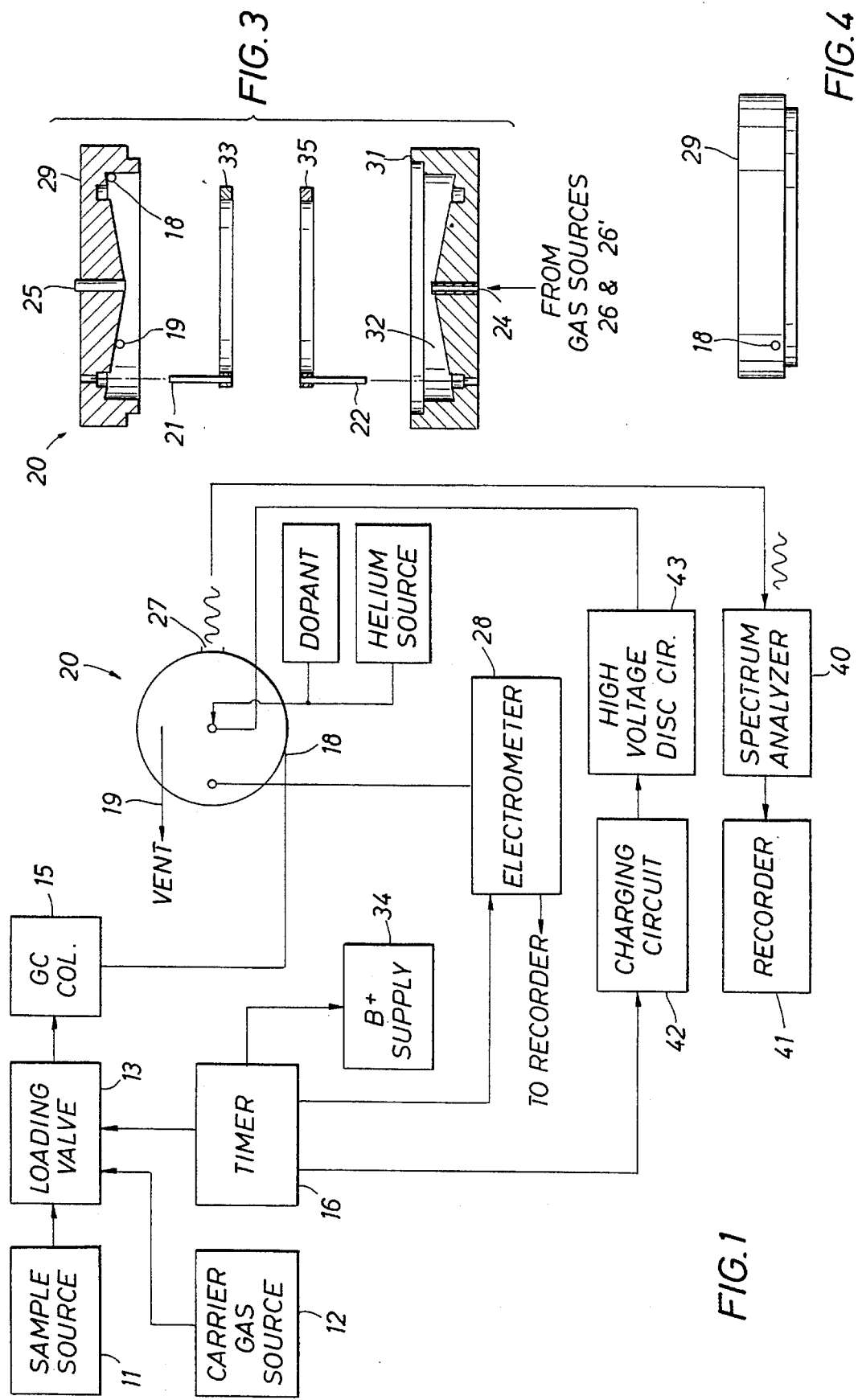
FIG. 1 is a system showing the cylindrical detector assembly of the present disclosure connected with a GC column and further shows the connected circuits which enable operation to provide several types of output data.

The present disclosure is directed to an ionization detector system connected with upstream and optional downstream equipment. The cooperative equipment defines one context for ease of explanation so that a thorough discussion of the spark detector system will provide the necessary explanation. This is a detector system devoid of radioactive apparatus and can be used in circumstances where radioactive materials are limited or forbidden. Heretofore, it has been common to operate electron capture devices with radioactive sources, the most common sources being tritium or nickel 63. Typically, these emit beta particles which trigger operation of the electron capture detector or perhaps helium ionization detectors. In this particular instance, a non-radioactive device is thereby provided. Noting FIG. 1 of the drawings, the numeral 20 identifies a detector system of the present disclosure. It will be described proceeding from the input in the fashion of a flow chart, and after that, certain features of the high voltage DC powered pulsed spark discharge system will be discussed, and its interaction with various types of detector systems including charge measuring devices and spectrum analyzers will also be set forth. Certain equations will be given which are believed to correctly describe the nature of the particles of the process. At this stage, the detector will be described with a GC column, and its operation will be given with various inputs.

The present detection system utilizes a carrier gas source 12 connected to the detector with an input valve (not shown). The source provides a carrier gas flow and a sample will be discussed later; there is a constant flow delivered into and through the detector at a controlled pressure and flow rate. Briefly, a carrier gas is supplied in a steady flow rate and pressure. Representative sample compounds may include various and sundry halo carbons and other organics which are carried with the flowing carrier gas. For representative purposes, a specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. It is preferable that the sample AB be delivered with argon as the carrier gas. While several gases can be used, the preferred carrier gas is He with argon. Purity will be discussed below. The gas flow is directed to an inlet opening of the plasma detector 20.

A trace element dopant may optionally introduced into the chamber by means which will be described later. A suitable dopant material is $N_2$ which is provided in a controlled quantity, such as one to one thousand parts per million. A typical range for this dopant can be from one part in $10^3$ to one part in $10^9$. The compound AB flows with the carrier gas into the chamber and ultimately interacts charged particles. The spark is formed by current flow at a finite voltage; the spark does not fluctuate because the only mode of current flow is by means of a spark across the gap. The voltage necessary to achieve spark current flow is a function primarily of electrode spacing and tip geometry. The electrode tips are preferably fixed at a known distance from one another so that the voltage necessary to create the spark is fairly stable. Moreover, ambient pressure is maintained in the spark generator 20 so that the voltage does not vary with prevailing pressure. The charging circuit functions like a classic automobile ignition system in that a charging current is provided from a capacitor and coil. When the current flows, resistance breaks to the value required to sustain current flow and current flow then drops the stored electrical charge. Preferably, ringing in the supply circuit is suppressed. It should be noted that the pulse can have a substantial width, ranging down from many microseconds.

When current flows through the gap between the two spaced electrodes, particle excitation occurs. Among other things, elemental helium atoms are energized to become metastable helium and ultimately diffuses from the spark gap in the chamber in a fashion to be described. While a metastable helium atom may have an elevated energy level about twenty eV, it has a fairly long half life, and because of its size, relatively speaking, it diffuses somewhat slowly. The metastable helium atoms will diffuse at some slow rate in all possible directions. This diffusion rate and range can be enhanced depending on housing geometry and detector electrode geometry, placement and voltage. Moreover, when the pulse occurs, there is a substantial electron discharge into the carrier gas atmosphere from the gap, and is quite high. That is, electrons are emitted from and distributed into the immediate atmosphere. These electrons can be observed throughout the detector 20.

There are several equations which are helpful to describe the relatively simple sequence of events occurring in the detector 20. Recall again that flow is circular, diffusion of the charged particles from the spark gap can be initiated and controlled by choice of polarity and potential on the detector electrodes 33 and 35. Indeed, the mobility of electrons :is substantially instantaneous to the extent that electrometer response can be observed promptly even though the spark has a width of less than one microsecond, perhaps a width of only 10 to 300 nanoseconds. The nearly instantaneous diffusion of electrons primarily results from their extreme mobility in comparison with larger charged particles, namely, the metastable helium. Regarding the spark, the voltage across the terminals is typically several thousand volts prior to current flow; once current flow begins, the voltage across the terminals rapidly changes as current flow changes from the initial zero value toward the peak current and then decays. The pulse shape is relatively easy to define at the start of the pulse but it may be difficult to define at the end of the pulse. There are, two reasons for this; the first reason is that the power supply may ring and provide post pulse current reversals. This is preferably suppressed by incorporating means to damp the ringing. A second reason is more subtle, and relates to the ionized particles between the electrodes during the pulse. The resistance across the electrodes may be very low, perhaps so small that it permits current (ionized particles) between the electrodes instantaneously observed at the facing electrodes even though the power supply, at that instant, provides no voltage.

Figure 2:
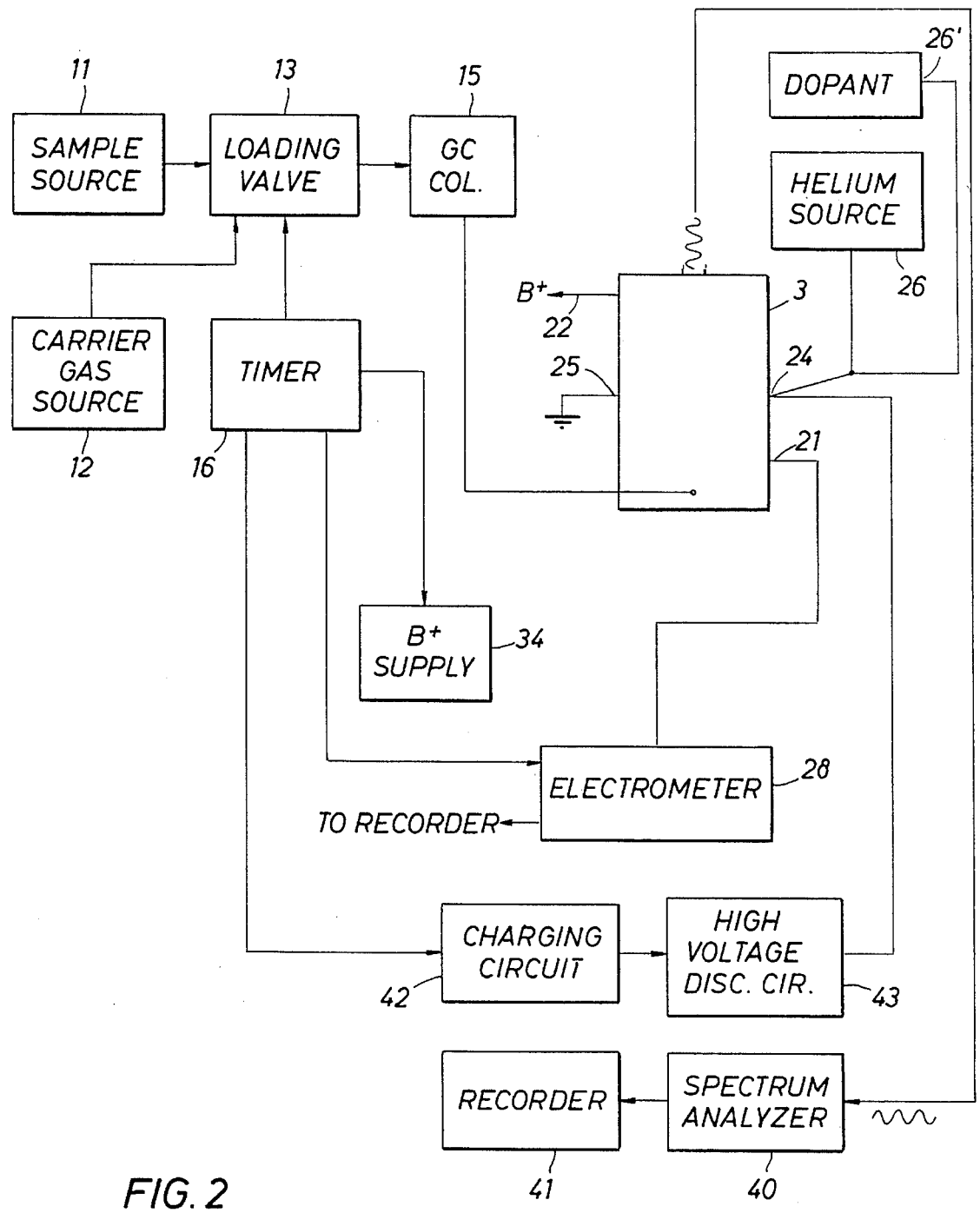
FIG. 2 is a view similar to FIG. 1 showing a side view of the cylindrically shaped detector assembly.

FIG. 2 shows the present detector 20 in a representative GC system which utilizes a sample source 11 and a carrier gas source 12 which are both connected with a loading valve 13. They provide a carrier gas flow at a constant flow delivered at a controlled pressure and flow rate to a 6C column 15. There is a system timer 16 which controls the operation of certain components as will be set forth. Briefly, a carrier gas is supplied in a steady flow for the GC column. Representative compounds include various and sundry halocarbons and other organics which are supplied with the flowing carrier gas through the loading valve 13 to the GC column 15. A specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. The discharge of the GC column 15 is directed to the inlet opening 18 of the detector 20.

In FIG. 1, the sample source 11 is input into a loading valve 13. The loading valve switches a selected or quantified portion of sample which is delivered to a GC column 15. The sample is supplied by a carrier gas flow from the source 12. Operation of the loading valve 13 is controlled by a timer 16. As shown in FIG. 1, the GC column provides a discharge which is delivered into the detector 20. There is a tangential inlet port 18. That port is directed to the interior to initiate rotational motion. Discharge is through a vent port 19. These two ports can be arranged opposite each other, and by positioning them at different distances from the center. More will be noted regarding this later. There are two ring shaped electrodes as will be described with respect to FIG. 3. One of the electrodes is the collecting electrode which is provided with a terminal 21. That terminal is connected to the electrometer 28. As better shown in FIG. 2 of the drawings, the terminal 21 connects with one ring electrode while the terminal 22 connects with another electrode which serves as a bias electrode. More will be detailed regarding these in a description of FIG. 3. A B+ supply 34 provides power for various components. Because the system can operate with timed operation, one output from the B+ supply 34 is directed by the timer 16 to a charging circuit 42. The charging circuit operates in conjunction with a high voltage discharge circuit 43 which forms an output current in the shape of a controlled polarity, controlled width and, specified current flow. This is delivered to a first inlet terminal 24 opposite a ground terminal 25. The terminals 24 and 25 provide the DC spark in the interior of the detector 20 as will be described. Preferably, one of the two terminals is hollow. Alternately, it can be constructed with a simple point which is surrounded by an axial passage for delivery of helium from a helium source 26.

Another aspect of the present apparatus, it is shown in both FIGS. 1 and 2 to incorporate a window 27 which enables light to be emitted from the spark, and that is observed by a spectrum analyzer 40. The analyzer 40 provides an output signal to the recorder 41. The light emissions for operation of the device are transmitted out of the system through the window 27. This window is made of material which is impervious to the irradiation created within the detector 20.

Considering now FIGS. 1 and 2 jointly, it will there be observed that a continuous flow of helium is delivered at the center of the detector 20 through the hollow electrode 24. Helium is supplied from the reservoir 26. Dopant may be optionally introduced from the reservoir 26' into the helium flow prior to entry into the detector through the hollow electrode 24. This central input of helium and optional dopant does not cause rotation. Rather, rotation is initiated by the tangential gas flow. This is based primarily on the carrier gas flow from the GC column 15. That gas flow is introduced at a tangent to initiate rotation. Consider now the relative weights of the gases that are introduced. Assume for purposes of discussion that the carrier gas in argon. Argon is heavier than helium. If helium is introduced from the source 26 at a centerline location, it will diffuse radially outwardly only as permitted by the heavier swirling argon carrier gas. If a steady flow of argon is introduced, it will establish rotation in the housing which is a circular flow path. This circular flow path is controlled in velocity by the relative flow rates, the relative size of the detector interior, the difference in the molecular weights of the various gases and by centrifugal forces acting upon the gas molecules. For instance, a heavier carrier gas will rotate with a greater velocity and will tend to stratify, thereby keeping the lighter helium gas toward the center of the housing and the heavier sample gases away from the spark electrodes 24 and 25. This minimizes contamination and corrosion of the spark electrodes. This can be used to advantage so that the flow of helium is relatively small.

Going now to FIG. 3 of the drawings, the detector housing 20 is shown as two cylindrical shell portions. One shell portion 29 incorporates a circular protruding lip 30 which enables the shell half 29 to nest against and join with a second shell portion 31. The shell portions 30 and 31 join together with an overlapping lip arrangement. The two shell portions join together so that a chamber 32 is formed on the interior. The rings for the electrodes are likewise shown. The collecting electrode 21 is connected to a ring 33 while the similar ring 35 is the bias electrode. The two rings are spaced towards the outer cylindrical edge of the circular chamber. The rings are mounted so that they are located in the cylindrical space 32. They are close to each other but there is a gap between the two. As will be understood, the housing portions 29 and 31 are formed of a material of which is not an electrical conductor. Going now momentarily to FIG. 4 of the drawings, the shell portion 29 is again shown and is provided with a tangentially located inlet passage 18. The passage 18 is formed at right angles to the view of FIG. 4. It therefore introduces gas flow just at the interior tangential edge of the cylindrical chamber. As will be observed in FIG. 3 of the drawings, the port 18 is for gas flow introduction. The port 19 is a vent. It can be located radially inwardly as illustrated in FIG. 3. Placement of these two with respect to the radial separation from the centerline axis of the structure and with respect to the two collecting electrodes is a design factor which can be varied so that gas flow in the system can be directed between the two electrodes. The two electrodes can be swapped; they can be located at a common or different radial spacings from the centerline.

DESCRIPTION OF CHARGED PARTICLES AND THEIR REACTIONS

There are several results which occur as a result of the spark discharge through the spark gap. For one, the pulsed spark discharge causes immediate energization of molecules (atoms of helium) in the gap. The mechanism apparently involves collision of the high energy electrons in the spark gap with the helium molecules. In addition to that, molecules (again atoms of helium) in the gap may subsequently emit radiation in a unique spectral distribution characteristic of the excited species and hence form characteristic emission spectra. The several processes occurring during the spark discharge can be summarized by the following five different reactions:

$$e^- + AB \rightarrow AB^+ e^- \tag{1}$$

$$e^- + AB \rightarrow A + B^+ + e^- \tag{2}$$

$$e^- + AB \rightarrow AB^* + e^- \tag{3}$$

where $AB^* \rightarrow AB + h\gamma$ $$e^- + AB \rightarrow A + B^* + e^- \tag{4}$$

where $B^* \rightarrow B + h\gamma$ $$e^- + AB \rightarrow (AB^+)^* + e^- \tag{5}$$

where $(AB^+)^* \rightarrow AB^+ + h\gamma$ where $e^-$ denotes a free electron, "*" denotes an atom in an excited state and "+" denotes an ionized atom.

Another reaction which occurs as a result of the pulsed high voltage spark discharge is the conversion of helium into high energy metastable atoms having an energy of about nineteen eV. This reaction is given in Equation 6:

$$e^- + He \rightarrow He^* + e^- \tag{6}$$

In the foregoing He* represents the metastable helium atom just as the * above in Equations 3, 4 and 5 represents an enhanced energy level for the particular molecule represented by the symbol AB. In the case of metastable helium, it has a relatively long life, depending on the pressure, and the enhanced energy state has sufficient energy to cause subsequent reactions. Equations 7, 8, 9 and 10 describe selected reactions which can occur involving the metastable helium. As will be understood, the metastable helium extends the duration of the process long after the spark discharge is terminated. In fact, the metastable duration can be hundreds of milliseconds while the spark duration might be only a few nanoseconds. The equations below describe various ionization or excitation results from the metastable helium which results are quite different from those initially caused by the high voltage spark discharge set forth in Equations 1–5 above. Accordingly, Equations 7–10 generally summarize the following reactions resulting from the metastable helium.

$$He^* + AB \rightarrow AB^+ + e^- + He \tag{7}$$

$$He^* + AB \rightarrow A + B^+ + e^- + He \tag{8}$$

$$He^* + AB \rightarrow AB^* + He \tag{9}$$

where $AB^* \rightarrow AB + h\gamma$ $$He^* + AB \rightarrow A + B^* + He \tag{10}$$

where $B^* \rightarrow B + h\gamma$

Equations 3, 4, 5, 9 and 10 all describe reactions which form specific and characteristic emission spectra, thereby providing a characteristic signal which enables analysis of the emission source. However, one set of spectra will be emitted after the spark in view of the longer decay times involved, for example, in the last four equations above.

Building on this, a sequence of operations will be described. This involves pulsing the high voltage supply to obtain the appropriate narrow pulse so that certain phenomena occur during the spark, and other phenomena occur after the spark, enabling analysis of different emission spectra at different times relative to the spark and its duration. Discussion of these timing factors can also be tied to a discussion of scaling factors relating to particular voltages.

Measurement of a particular charged species is normally made remote from the spark gap. Carrier gas flow in a circle at a specified rate is a scale factor which relates to system sensitivity. Moreover, system sensitivity is controlled by adjustment of the $B^+$ voltage (positive or negative) applied to the bias electrode 35. Also, sensitivity is impacted by the radial spacing from the spark gap. Timing is an important scale factor. Consider a typical example. When detecting ions larger than electrons, the detection pulse is applied for a longer interval of time to detect ionic dispersion from the spark gap. Thus, the compound AB forms ionic particles which are measured by periodically pulsing the $B^+$ for detection. Assume a pulse of twenty microseconds down 10 to 200 nanoseconds. The spark causes ions to form and the charged particles (less mobile than electrons) drift to the vicinity of the appropriate electrodes. This movement is influenced by the geometry and voltage on the several electrodes. The electric field formed by the two ring electrodes controls charged particle dispersion toward the collecting electrode. The electrometer 28 measures the impingement of electrons at the ring shaped terminal and forms an output current. This can be repeated in cyclical fashion. For instance, the DC pulse can be repeated with a pulse spacing of one millisecond. The compound AB is in the detector chamber for a relatively long period of time due to the circular motion of the flow. Using the relatively long duration in which a compound AB is in the detector system, this assures that the peak will be sampled many times. For instance, assume that the GC column eluate discharges the AB compound over a two second interval. Assume further that the next compound is discharged over a four second interval. Assuming the first eluate transit time through the detector 20 is equal two seconds, over 2,000 samples for that peak will be obtained. The 2,000 data points thus encode the data to assure that proper measurement is obtained and is output to the recorder 41.

As will be observed in the foregoing, the current measured from the charged particles (whether small, highly mobile electrons or larger and less mobile ions) can be timed or gated so that detection of one species can occur during the spark and for a very short duration thereafter, or alternately, long after the spark is terminated. Because of the differences that result during the spark versus the reactions occurring after the spark, the phenomena represented by Equations 1–10 above are different and can be distinguished by observation either of the concentration of electrons or ionized particles or by observation of the different emission spectra. Moreover, the emission spectra is different at different times within the detector. For instance, one emission spectra is observed during the spark and another is observed later.

One valuable benefit of the present apparatus is use of the pulsed high voltage spark discharge as an ionization detector devoid of radioactive sources. This can be done either by using the electron burst during the discharge or the ionization after the discharge resulting from the metastable helium atoms. The ionization initiated responses are thus quite different, and they can be used as a qualitative test of suspected compounds. So to speak, the pulsed system performs as two separate detectors testing the compound AB repetitively, providing two output signals which can be separated and yet which correlate to enhance GC peak analysis.

If desired, the pulsed high voltage spark discharge system 20 can be used in an electron capture detector devoid of a radioactive source. The helium gas can be provided with a dopant gas; the preferred dopant is $N_2$ which creates a relatively high standing current as a result of ionization of the $N_2$. In the event the eluated molecule tends to capture electrons, the standing current flow through the device will decrease in proportion to eluated molecules introduced into the chamber.

Connected upstream and downstream devices are important in use of the detector 20. For instance, in a manufacturing plant, a single compound AB can be tested repetitively. A variety of unknown compounds can be tested with GC separation as mentioned. The present detector can be connected by any suitable supply system to enable testing and quantification of one or more compounds. The detector output is alternately furnished by the current flow from the electrode 27, or is optically determined by the spectrum analyzer. In both instances, the data is potentially different during the pulse and after the spark. This enables an entirely different measurement to be obtained.

One mode of use of the present apparatus is as an ionization detector. In that instance, the bias electrode can be omitted. The collector electrode is provided with negative voltage. A representative voltage might be −100 volts, extending to perhaps −250 volts. A DC voltage is placed on this electrode. In that instance, the structure can be used as an ionization detector.

The structure shown in FIG. 2 can be used in different fashions. Primarily, the differences relate to the voltages which are placed-on the ring electrodes. The electrodes can be made positive or negative. The system thus can be used as an electron capture detector by using illustrated electrodes 33 and 35. Alternately, it can be used in a different fashion simply by disconnecting the electrode 33, or optionally by removing the electrode 33. Operation of the device becomes variable dependent on the interplay of several important factors. One important factor is the position of the GC sample inlet 18. As the tangent angle is varied, sensitivity of the system is also varied. Another important factor is the choice of positive or negative voltage on the terminal 33. This electrode has an influence on the flow of metastable helium which interacts with the introduced gaseous sample. Another factor is the voltage on the electrode 33. Finally, the presence or absence of a dopant gas should be noted. As a generalization, it provides even further: variation in system operation.

The detector 20 is usually operated at ambient temperature, or it can be operated at raised temperatures of up 300° C. The pressure within the chamber is essentially equal to atmospheric pressure. The helium flow typically is less than 10 cubic centimeters per minute. As mentioned, ratios were given for the dopant gas which is added optionally as mentioned. Finally, another scale factor which is varied is the duty cycle of the pulse, and it is varied in accordance with any suitable sequence. The spark is the source of the metastable helium which decays over an interval to provide the necessary energy for interaction with sample molecules and subsequent detection at the electrometer electrode.

IMPROVED OPTICAL MEASURING SYSTEM

The cylindrical shell or housing defines an internal mixing chamber. The housing is formed of material which is opaque to light emissions. It does however have a single shielded window 27. The window is formed of an appropriate material to pass a wave length of interest. The wave length of interest is selected for the region of investigation. As known, the visible light spectrum is approximately 4,000 to 7,000 A°, and that frequency range can be selected. There are reasons to select other frequency ranges; frequency ranges outside the visible spectrum can also be chosen. Appropriate for the frequency range, a particular material is chosen for the window 27 so that it is essentially transparent to that particular frequency range.

A sample of interest is introduced through a GC system and delivered into the chamber 20 through the inlet 18. The GC gas sample mixes with the helium in the chamber 20. The ratio of the sample to the helium is a scale factor which is determined by the flow rates of the sample and the helium. It is also determined in part by the volume of the chamber 20. Suffice it to say, these are scale factors which can be modified to achieve a particular ratio on mixing the sample with the helium gas.

The inlet 18 is tangent to direct the sample flow away from the window 27. The sample typically does interact with the material forming; the window. The electrical spark interacts with the helium and sample to provide optical emissions. They are normally scattered in all directions. Of particular importance to the present apparatus, the optical emissions are observed in the window 27 and are transmitted through the window. The window is able to transmit the optical emissions to the optical measuring device on the opposite side of the window. This is accomplished in the desired fashion so that the optical measuring instrument can observe the emissions and make the necessary measurements. For instance, one form of measurement is detection of the frequency or wave length of particular emissions, and another measurement is the duration and intensity of such emissions. These measurements typically are made by the optical measuring instrument after transmission through the window 27. The window is protected from chemical damage. It is not uncommon that the window surface exposed to the chamber 20 will either become etched or at least smudged with materials derived from the sample in the chamber especially after the sample is highly energized. In this particular instance, the embodiment 20 is configured so that the GC sample is removed from the chamber rather quickly and the exhaustion of any highly activated sample material protects the window 27. It is not unreasonable to suggest daily cleaning of the window in systems where the window is in contact with the sample after it has been energized in the spark. For instance, windows are normally installed for easy removal so that they can either washed or otherwise cleaned for clearing the window of any film or smudge which might obscure optical transmission. Suffice it to say, this type arrangement is protective of the window and enables the equipment to operate with better optical transmission for longer intervals.

While the foregoing is directed to the preferred embodiments, the scope thereof is determined by the claims which follow.

What is claimed is:

1. A charged particle detector comprising:
   (a) a circular closed chamber having a gas flow inlet and spaced outlet positioned to direct gas flow through said chamber and said chamber directs the gas flow in a circle therein;
   (b) spaced electrodes provided with a current sufficient to enable an electrical spark to be formed in a gap between said electrodes locating the spark thereacross, said electrodes being positioned to form a spark in gas in said chamber to create charged particles; and
   (c) a spaced detector electrode in said chamber for collection of charged particles wherein the charged particles move to said detector electrode to form a current indicative of a sample gas concentration in said chamber.

2. The apparatus of claim 1 wherein a sample gas is diffused with charged particles in said chamber.

3. The apparatus of claim 2 wherein said gas glow comprises helium atoms having an excited high energy metastable state with transitions to a lower energy state, and thereby interact with the gas sample.

4. The apparatus of claim 1 wherein said detector electrode is spaced circumferentially from said spark forming electrodes, and at least one bias electrode is connected to a voltage source to control charged particle impingement thereon.

5. The apparatus of claim 1 wherein said spark forming electrodes are periodically pulsed with DC current to form a DC spark during pulsing wherein the spark forms an incandescent current flow across said gap, and said spark electrodes are flush mounted in a surrounding circular housing of non-conductive material to direct gas flow in circular movement.

6. The apparatus of claim 1 wherein said chamber is cylindrical and a gas sample is introduced at a tangent to initiate gas flow.

7. A method of analyzing a sample compound comprising the steps of:
   (a) flowing a sample compound gas in a circle in a confined chamber;
   (b) forming energized particles to impinge on the gas flowing in a circle;
   (c) mixing the energized particles with the gas to disperse the energized particles into the gas for measurement of the gas within the chamber; and
   (d) wherein the measurement step is after mixing the sample gas compound with energized particles.

8. The method of claim 7 wherein an inert gas capable of being changed to a metastable state is exposed to a spark, and the metastable state is sustained for a time interval.

9. The method of claim 8 wherein the gas is helium and forms metastable helium; and further wherein the gaseous sample provides sample molecules for measurement.

10. A gas detector for identification and quantification of sample compounds, comprising:
    (a) a circular chamber having a tangential chamber inlet and a tangential outlet, and a circular gas flow path between said inlet and outlet ends;
    (b) means for flowing an inert gas into said chamber;
    (c) two spaced electrodes locate din said chamber to produce repeated current sparks across said chamber wherein gas interaction forms energized particles in the chamber;
    (d) a sample source connected to deliver gas into said chamber; and
    (e) means responsive to interacted sample gas and charged particles to enable sample gas detection in said chamber.

11. The apparatus of claim 10 wherein a dopant is added into the chamber by a dopant supply means to provide a source of thermalized electrons to measure electron capture.

12. The method of claim 7 wherein said measuring step comprises the steps of providing a charge collecting electrode within said chamber which is radially spaced from discharge electrodes in said chamber, forming an electric field within said chamber for attracting electrons produced in said chamber as a result of said electrical discharges passing through said carrier gas, measuring charge attracted to said charge collecting electrode substantially during the time of said periodic electrical discharges and indicating the measured current, measuring charge attracted to said charge collecting electrode during the time between said periodic electrical discharges and indicating the measured current, as an indicator of a characteristic of said sample gas.

13. An electron capture detector comprising:
    (a) a closed chamber having a helium flow inlet to enable helium flow therethrough;
    (b) spaced electrodes forming a spark between said electrodes defining a spark thereacross, said electrodes being positioned in said chamber to form a spark through helium in said chamber;

(c) a sample gas source connected to an inlet to said chamber to provide sample gas flowing in said chamber and said chamber and said inlet are constructed and arranged to flow gas in a circle in said chamber;

(d) a spaced detector in said chamber for collection of current formed as a result of the spark across the gap wherein the spark irradiated helium enables a current to be formed indicative of eluated gas sample concentration in said chamber; and (e) wherein the detector measures the gas sample in said chamber by change in current flow.

14. The apparatus of claim 13 wherein said chamber is a circular hollow chamber enabling circular flow.

15. The apparatus of claim 14 wherein said chamber is defined by a pair of facing housing walls extending to a circular, surrounding wall.

16. The apparatus of claim 15 including a tangential flow passage into said circular chamber.

* * * * *